United States Patent [19] [11] Patent Number: 4,844,089
Roberti [45] Date of Patent: Jul. 4, 1989

[54] NEEDLE FOR MULTIPLE VACUUM BLOOD SAMPLE DEVICES

[76] Inventor: Lamberto Roberti, Via Bonini, 140, 6100 Pesaro, Italy

[21] Appl. No.: 153,836
[22] PCT Filed: May 13, 1987
[86] PCT No.: PCT/IT87/00044
 § 371 Date: Jan. 14, 1988
 § 102(e) Date: Jan. 14, 1988
[87] PCT Pub. No.: WO87/06813
 PCT Pub. Date: Nov. 19, 1987

[30] Foreign Application Priority Data
May 14, 1986 [IT] Italy ................................. 4883 B/86
Dec. 30, 1986 [IT] Italy ................................. 3627 A/86

[51] Int. Cl.⁴ ............................................. A61B 5/00
[52] U.S. Cl. .................................. 128/764; 604/205; 604/239; 604/264
[58] Field of Search ...................... 128/760, 762–771; 604/192, 197–199, 200–202, 205, 239, 263–264

[56] References Cited
U.S. PATENT DOCUMENTS

| 3,326,206 | 6/1967 | Barr, Sr. et al. | 604/239 X |
| 3,434,468 | 3/1969 | Barr | 604/239 X |
| 3,494,352 | 2/1970 | Russo et al. | 128/764 |
| 3,520,292 | 7/1970 | Barr | 128/764 |
| 4,150,666 | 4/1979 | Brush | 128/763 |
| 4,409,990 | 10/1983 | Mileikowsky | 128/763 |
| 4,444,203 | 4/1984 | Engelman | 128/763 X |

Primary Examiner—Kyle L. Howell
Assistant Examiner—Angela D. Sykes
Attorney, Agent, or Firm—Laff, Whitesel, Conte & Saret

[57] ABSTRACT

An improved needle for multiple vacuum blood sample devices, consisting in two opposed, coplanar needles connected by an oblique member and protected by a rigid sheath such that the relevant test tube holder is not coaxial to the needle to be introduced in the vein; the second needle is angled with respect to the geometrical axis of the test tube so that the outflowing blood strikes only against only the side wall of the test tube, and with the minimum angle of incidence.

6 Claims, 1 Drawing Sheet

NEEDLE FOR MULTIPLE VACUUM BLOOD SAMPLE DEVICES

BACKGROUND OF THE INVENTION

The present invention relates to an improved needle for multiple vacuum blood sample devices, of the type that pointed at both opposite ends to form two needles, fitted with relative covering elements, the first of which is designed to be introduced to the epidermis and vein, the second to be introduced into the closing stopper of a test tube, the needle in addition featuring, in what is substantially its central portion, an element for joining and retaining the covering element, and a threaded body, designed to engage in a corresponding hole centred in a test-tube carrying cylinder fitted with horizontally disposed tangs at either side to be gripped by the index and middle fingers of the user's hand.

As is well known in medical technique, blood samples for tests are taken using common syringes fitted with a hollow needle that draws the blood out of the vein.

Simple as these operations might seem when carried out by an expert, it is occasionally not so easy to introduce the needle without passing right through the vein, this making it necessary for the operation to be carried out again from the start.

The above happens as a result of the fact that the syringe will always take up a certain amount of space, obliging the operator to effect the injection and, above all, introduction into the vein, with a certain angle of incidence relative to the surface of the epidermis.

Syringes also exist that have an offset, or eccentric point for attachment needle: in such cases it is easier for the blood to be drawn out, but it can only be transferred to the test tube after the syringe has been withdrawn from the vein. However, more than one test will often be carried out, and it is thus necessary for several samples to be taken and divided between a similar number of test tubes. This forces one to use notably large syringes in order to take the necessary quantity of blood in one operation, and subsequently fill the single test tubes.

The problem of the angle of incidence of the needle, and that of taking multiple blood samples, are both solved by the use of a device composed of a test tube carrying cylinder, known as a holder, designed to receive vacuum test tubes, of a first needle, held at one end by a small pipe featuring two flexible diametrical tangs enabling it to be gripped by hand, and of a second needle, which can be connected to the other end of the small pipe by means of a LUER cone, and its point inserted in static fashion within the test tube holder. This second needle is fitted with a rubber cap that covers it. The test tubes are closed under vacuum with rubber stoppers that are less thick in their centre portion in order to facilitate their being pierced by the second needle. Using this device, it is possible to introduce the first needle into the vein, practically parallel to it, inasmuch as the space taken up by its diameter is almost negligible. It is then sufficient to place a test tube in the test tube carrying cylinder, pressing its stopper against the second needle which pierces it through the central zone of reduced thickness.

The full test can subsequently be replaced with another one without any problems, since the blood is retained by the cap of the second needle, which re-extends, completely covering the second needle, once the filled test tube has been removed.

A device constructed in this way reveals itself to be very practical in terms of ease of use, but has the disadvantage that there is a notable waste of valuable material -viz, the two needles, the LUER cone and small pipe, for every blood sample taken.

The greatest disadvantage, however, consists in the fact that the blood has to follow a long route from the vein to the test tube, with the possibility of minute clots being formed; these influence the results of the tests, above all in coagulationrelated tests such as the Quick time.

To eliminate these disadvantages, and above all that of the possible formation of small blod clots, consideration has been given to the use of double needles, that is to say, with two points, for introduction into the vein and introduction into the test tube stoppers respectively, fitted with a threaded element for connection to the test tube carrying cylinder, and featuring horizontally disposed tangs on which the index and middle fingers can locate and lay hold.

With this device, however, one gain has the problem of effecting a certain angle of inclination of the needle with respect to the epidermis.

The needle-epidermis angle problem also brings a functional problem in its wake, represented by the fact that, when in the vein, the point of the needle ends up being too close to the opposite wall of the vein. This means that, when the blood is being drawn out of the vein, this wall is also subjected to a certain amount of suction, such that it moves closer to and comes into contact with the point of the needle, and the operation of taking the blood sample is interrupted.

In this case, the provision of an offset, or eccentric connection for the test tube carrying cylinder cannot be contemplated, since the inner needle point (with cap) would not be able to pierce the centre portion of the test tube stopper, and piercing would be made difficult by the fact that the stopper wall is thicker.

In addition, there is another considerable problem: blood flows from the vein to the test tube at rather a high speed when using the vacuum test tube technique for taking blood samples, as a result of the difference in pressure between the two.

This speed is even higher at the start of the filling operation since, the vacuum being at its greatest, there is maximum suction. It is therefore possible on certain specific occasions, depending on the vacuum level in the test tubes, and the length of the tubes, for the out-flowing blood to strike against the bottom of the test tube, creating the conditions for a phenomenon commonly known as blood stress to arise.

Amongst the morphological components of the blood, one has erythrocytes, which are known to be composed of round-shaped cells covered by a thin membrane, and having a red-orange colour as a result of the hemoglobin contained within them.

When subjected to a mechanical action provoking the break-up of the membrane, the hemoglobin flows out and, mixing with the plasma, changes its transparency characteristics, thus making the results of certain common clinical tests unreliable.

The object of the invention is to eliminate all the aforementioned disadvantages, avoiding the possibility of the above disadvantages occuring, under any circumstances, whilst making the operation of taking multiple blood samples from a patient both easy to carry out, convenient, and practical.

SUMMARY OF THE INVENTION

The stated object is achieved with the present invention as a result of the special shape of the double type needle for multiple vacuum blood sample devices; this features two needles that are parallel but not coaxial, such that the axis of the test tube carrying cylinder and the axis of the needle to be introduced into the vein do not coincide.

According to the invention, the two needles lie in the vertical plane, perpendicular to the grip tangs of the test tube carrying cylinder.

A further object is achieved by the invention disclosed, namely, that the needle within the test tube is inclined with respect to the geometrical axis of the latter, in such a way as to optimize the impact of the blood against the wall of the tube when the blood sample is being taken.

BRIEF DESCRIPTION OF THE DRAWINGS

The invention will now be decriebd in detail, by way of example, with the aid of the accompanying drawings, in which.

DESCRIPTION OF THE PREFERRED EMBODIMENT

Figure 1:
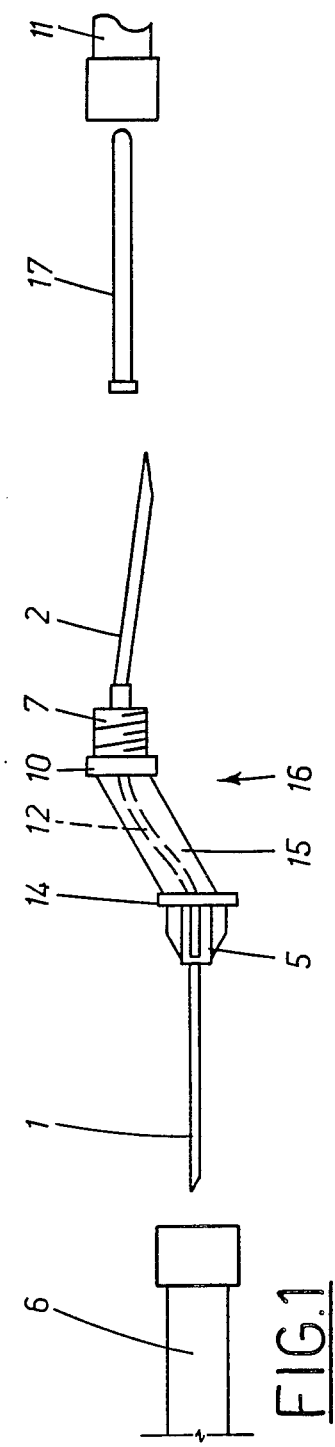
FIG. 1 is an exploded side elevation of the parts of the needle disclosed.

It can be seen clearly from the drawings that the needle, denoted 16 in its entirety, is of the double needle type, that is to say, with a point at either end, forming needles 1 and 2 respectively. Needle 1, the first of these two needles 1 and 2, is designed to be introduced into the epidermis, and subsequently into the vein, and the second, 2, to be introduced into a test tube carrying cylinder 9.

An element 5 is fitted to the needle 16 in a substantially central zone, joining and retaining an element 6 for covering the first needle 1, and a threaded element 7 featuring a ring-shaped body 10, preferably of cone frustum shape.

The threaded element 7 has two thread starts that are separated by 180° and designed to engage in the corresponding thread of a hole 8 centered with respect to the cylinder 9. The frusto-conical ring-shaped body 10 has a double function: to act as a stop against the outside edges of the hole 8, and to join and retain a second element 11 covering the needle denoted 2.

The test tube carrying cylinder 9 is designed to contain test tubes 4 that are closed under vacuum with respective stoppers 3, the wall of which is less thick in its central part and may easily be pierced by the second needle 2.

A rubber cap 17 is pulled over the second needle 2 and held fast by the threaded element 7.

According to the invention, the needles 1 and 2 are parallel with one another but not coaxial.

The needles 1 and 2 are connected to one another by a length 12 of material disposed obliquely to and connecting them. The needle 16 is bent in such a way that in the horizontal plane it lies perpendicular to the horizontal dimension of the grip tangs 13 on the test tube carrying cylinder 9, when the needle is fitted to the cylinder 9.

To best advantage, the retaining element 5 and threaded element 7 on the two sides of the oblique length 12 are connected to one another by means of an intermediate length 15 which covers and protects the oblique length 12.

A fluid-tight element 14, engaging with the covering element 6, is located between the retaining element 5 and the intermediate length 15.

Figure 2:
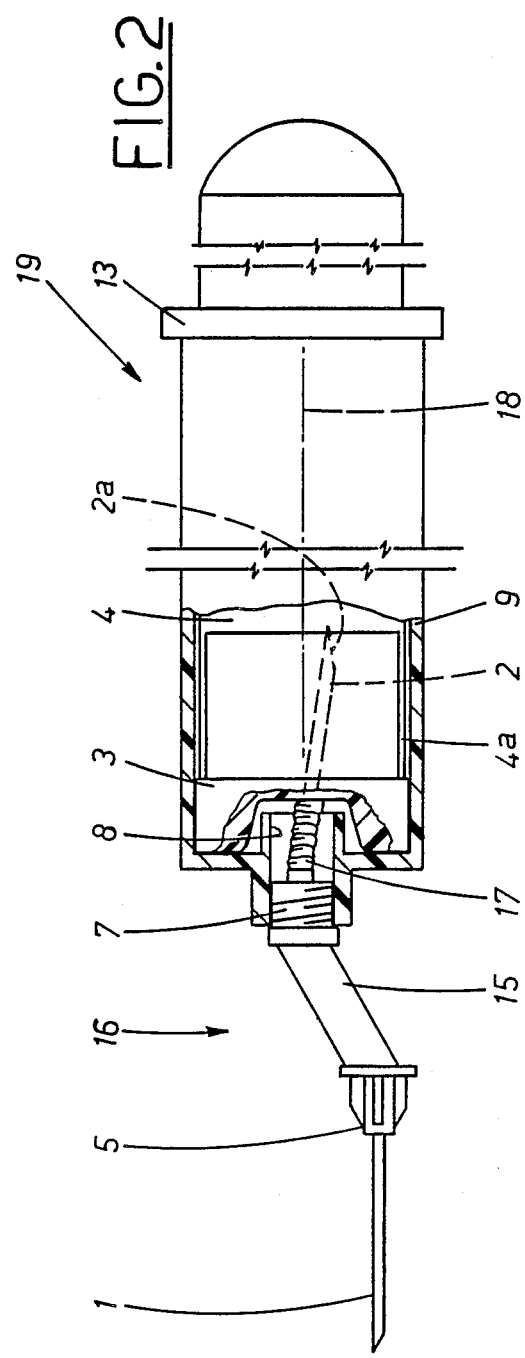
FIG. 2 is a side elevation of the needle with some parts shown in section better to reveal others, in which the needle disclosed is illustrated connected to a multiple vacuum blood sample device, ready to take a sample.

As shown in FIG. 2, the cap 17 is designed to be pushed up against the threaded element 7 when a test tube 4 is introduced into the test tube carrying cylinder 9. It performs its main function, however, when there is no test tube 4 associated with the carrying cylinder 9, by preventing blood from flowing out of the second needle 2.

It is now clear that the rigid length 15, being oblique, performs the role of shifting the needle 1 down and away from the axis of the carrying cylinder 9, enabling the blood sample device, denoted 19 in its entirety, to be positioned within the vertical plane passing between the axes of needles 1 and 2 such as to obtain the optimum angle of incidence in relation to the vein.

Although the needle denoted 2 is coplanar with the geometrical axis 18 of the test tube carrying cylinder or test tube, it is advantageously angled downwards with respect to the latter.

In addition, the needle 2 features a cut 2a, also running downwards, lying in a plane at a right angles to the vertical plane passing through the axes of the two needles 1 and 2.

The inclination of needle 2 makes it possible for the outflowing blood to strike only against the side wall 4a of the test tube.

It is obvious that by making the inclination of needle 2 compatible with the length of the test tube, such that the flow of blood strikes only the side wall 4a with the minimum angle of incidence, the inevitable impact against the test tube 4 can be softened to a degree that blood stress is prevented.

This effect is further reduced by the fact that the needle 2 faces downwards, that is to say, in the direction that decreases the number of possible impacts against the walls, whilst the direction of the cut 2a contributes to slowing down the flow, decreasing the energy of impact against the wall.

What is claimed:

1. A needle assembly for multiple vacuum blood sample device, comprising two needles, one at each end, parallel to one another but not coaxial, fitted with relative covering elements, the first needle being designed to be introduced into the epidermis and vein, and the second needle to be introduced into a closing stopper of a test tube, an element located substantially at center between the two needles, for connecting and retaining the first covering element, and a threaded body, designed to engage in a corresponding hold centered in a test tube carrying cylinder fitted with two horizontally placed tangs adapted to be gripped by the index and middle fingers of the hand an intermediate length disposed obliquely to and connecting the two needles, the second needle being inclined with respect to the longitudinal axis of the test tube in such a way as to strike only against its side wall.

2. A needle assembly as in claim 1, wherein the longitudinal axes of the first and second needles and of the oblique intermediate length lie in a vertical plane that is perpendicular to the tangs.

3. A needle assembly as in claim 1, wherein the intermediate length is located within a protective element placed between the connecting and retaining element, and features a ring-shaped edge for holding the first covering element, acting as a stop and holding the threaded body tightly engaged with the test tube carrying cylinder.

4. A needle assembly as in claim 3, wherein the ring-shaped body has the shape of a cone frustum.

5. A needle assembly as in claim 1, wherein the second needle is angled downwards and features a cut facing downwards and lying within a plane at right angles to the plane passing through the axes of the two needles.

6. A needle assembly as in claim 1, wherein the second needle is angled with respect to the axis of the test tube in such a way as to narrow the angle at which the blood strikes the side wall of the test tube as far as possible, the inclination of the needle depending upon the length of the test tube.

* * * * *